United States Patent [19]

Schaub et al.

[11] 3,978,097

[45] Aug. 31, 1976

[54] ETHER AND THIOETHER SUBSTITUTED 3,4-ALKYLENEDIOXYBENZENES

[75] Inventors: Fritz Schaub, Basel; Hans-Peter Schelling, Oberwil, both of Switzerland

[73] Assignee: Sandoz Ltd., Basel, Switzerland

[22] Filed: Aug. 6, 1973

[21] Appl. No.: 385,738

[30] Foreign Application Priority Data

Aug. 10, 1972 Switzerland............... 11840/72
June 8, 1973 Switzerland............... 8349/73

[52] U.S. Cl................ 260/340.5; 424/DIG. 12; 424/278; 424/282; 424/304; 424/308; 424/324; 424/331; 424/333; 424/337; 424/340; 424/341; 260/465 F; 260/465 K; 260/465 R; 260/470; 260/473 A; 260/558 S; 260/559 R; 260/592; 260/600 R; 260/611 A; 260/611 R

[51] Int. Cl.²............... C07D 317/06; C07D 317/44; C07D 323/02

[58] Field of Search................... 260/340.5; 424/282

[56] References Cited
UNITED STATES PATENTS 3,563,982 2/1971 Bowers ................... 260/340.5
3,825,661 7/1974 Emmick ................... 424/278

OTHER PUBLICATIONS

Chemical Abstract of German Offen. 2,161,150 (6–1972).
Chang et al., "Ag. Biol. Chem., vol. 35 (1971) No. 8, pp. 1307–1309.

*Primary Examiner*—V. D. Turna
*Attorney, Agent, or Firm*—Gerald D. Sharkin; Richard E. Vila

[57] ABSTRACT

The present invention concerns novel aromatic long chain alkenyl ethers and thioethers of the formula:

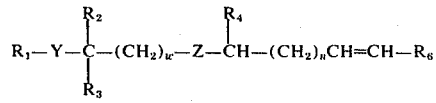

wherein
$R_1$ is a hydrocarbon group,
$R_2$, $R_3$ and $R_4$ are each H or alkyl,
$R_6$ is an aromatic radical,
Z is a divalent hydrocarbon group,
Y is *o* or *s*, and
*w* and *n* are zero or integers.

The compounds are useful insecticides and acaricides.

16 Claims, No Drawings

ETHER AND THIOETHER SUBSTITUTED 3,4-ALKYLENEDIOXYBENZENES

The present invention relates to ethers and thioethers and more specifically to aromatic long chain alkenyl ethers and thioethers which possess insecticidal and acaricidal properties.

The present invention provides compounds of formula I,

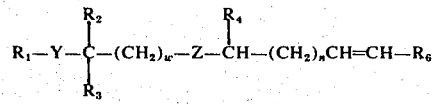

wherein
- $R_1$ is alkyl of 1 to 6 carbon atoms, alkenyl of 3 to 6 carbon atoms, alkynyl of 3 to 6 carbon atoms, cycloalkyl of 5 to 7 ring carbon atoms or cycloalkyl of 5 to 7 ring carbon atoms substituted by alkyl of 1 to 6 carbon atoms,
- $R_2$, $R_3$ and $R_4$ are each, independently, hydrogen or alkyl of 1 to 4 carbon atoms,
- Z is a divalent group $-CR_5=CH-$, $-CH=CR_5-$ or $-CH-R_5-$
  - wherein $R_5$ is hydrogen or alkyl of 1 to 4 carbon atoms,
- Y is oxygen or sulphur,
- $w$ and $n$ are, independently, zero or an integer 1 to 4, and
- $R_6$ is an aromatic radical $Ar_1$

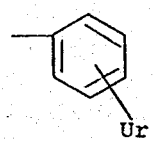

or an aromatic radical $Ar_2$

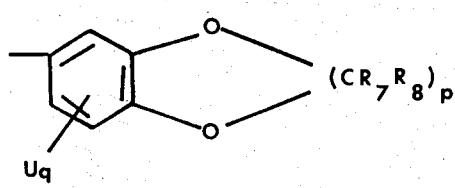

wherein
U is alkyl of 1 to 6 carbon atoms, alkenyl of 2 to 6 carbon atoms, alkoxy of 1 to 6 carbon atoms, alkenyloxy of 3 to 6 carbon atoms, formyl, alkylcarbonyl of 2 to 6 carbon atoms, alkoxycarbonyl of 2 to 6 carbon atoms, carbamoyl mono- or di-substituted by alkyl of 1 to 6 carbon atoms, alkoxymethyl of 2 to 7 carbon atoms, alkylthio of 1 to 6 carbon atoms, cyano, nitro, chlorine, bromine or phenyl, $R_7$ and $R_8$ are, independently, hydrogen or alkyl of 1 to 6 carbon atoms,
$r$ is an integer 1, 2 or 3,
$p$ is an integer 1 or 2, and
$q$ is zero or an integer 1 or 2.

It is to be understood that when either $r$ or $q$ is an integer greater than 1, then the multiple substituents U on the benzene ring may be the same or different.

Unless otherwise indicated, it is to be understood that when any or all of $R_1$, $R_2$, 3, $R_4$, $R_5$, $R_6$, $R_7$, $R_8$ or U are, or include, aliphatic hydrocarbon groups of more than 2 carbon atoms, then the aliphatic group may be straight or branched chain, a primary or a secondary group, or when of more than 3 carbon atoms, then the aliphatic hydrocarbon group may alternatively be a tertiary group.

When $R_1$ is alkyl, this is preferably alkyl of 2 to 6 carbon atoms, particularly of 3, 4, 5 or 6 carbon atoms, especially isopropyl, sec. butyl or isopentyl, i.e. generally secondary or branched alkyls.

When $R_1$ is alkenyl, this is preferably of 3, 4 or 5 carbon atoms, e.g. allyl, 3-buten-1-yl and 4-penten-1-yl, particularly allyl.

When $R_1$ is alkynyl, this is preferably of 3, 4 or 5 carbon atoms, e.g. 2-propyn-1-yl, 3-butyn-1-yl and 4-pentyn-1-yl.

When $R_1$ is, or contains, cycloalkyl, this is preferably cyclohexyl.

When $R_1$ is cycloalkyl substituted by alkyl, this is preferably cycloalkyl substituted by alkyl of 1, 2, 3 or 4 carbon atoms, especially methyl, ethyl or n-propyl, e.g. methylcyclohexyl, ethylcyclohexyl or n-propylcyclohexyl.

Preferably, $R_1$ is alkyl of 1 to 6 carbon atoms.

When any of $R_2$, $R_3$, $R_4$ or $R_5$ is alkyl, this is preferably of 1, 2 or 3 carbon atoms, particularly methyl, ethyl or n-propyl, especially methyl or ethyl.

Preferably one or both of $R_4$ and $R_5$ is alkyl of 1 to 4 carbon atoms.

When U is, or includes, an aliphatic hydrocarbon group, this is preferably of less than 6 carbon atoms, more preferably less than 5 carbon atoms, e.g. of 2, 3 or 4 carbon atoms. Thus, when U is alkyl, this is preferably of 1 to 4 carbon atoms, e.g. methyl, ethyl, n-propyl or n-butyl particularly of 1 to 3 carbon atoms, more particularly methyl or ethyl. When U is alkoxy or alkylthio, this is preferably of 1, 2, 3 or 4 carbon atoms, e.g. methoxy, ethoxy, n-propoxy or n-butoxy, or, methylthio, ethylthio, n-propylthio or n-butylthio, particularly methoxy or ethoxy, or, methylthio or ethylthio.

Preferably, U is alkyl, alkoxy or alkylthio, especially alkyl or alkylthio.

When $R_7$ or $R_8$ is alkyl, this is preferably of 1, 2, 3, 4 or 5 carbon atoms, particularly methyl or ethyl.

Preferably one or both of $R_7$ and $R_8$ are hydrogen.

The present invention also provides a process for the production of a compound of formula I, which comprises:
a. splitting off HX
wherein
X is a leaving group, from a compound of formula II,

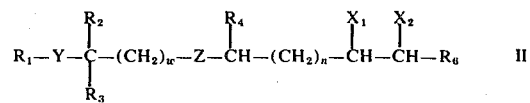

wherein
- $R_1$, $R_2$, $R_3$, $R_4$, $R_6$, Y, Z, w and n are as defined above, and
one of $X_1$ and $X_2$ is hydrogen and the other is X, wherein
X is as defined above, being preferably —OH, Cl, Br, I, alkyl-sulphonyloxy of 1 to 6 carbon atoms or arylsulphonyloxy of 6 to 12 carbon atoms, e.g. phenylsulphonyloxy,
by an elimination reaction,
b. selectively condensing a compound of formula III

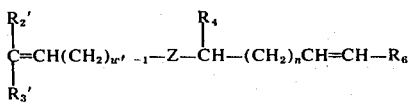   III wherein
$R_4$, $R_6$, Z and n are as defined above,
$R_2'$ and $R_3'$ are each, independently, alkyl of 1 to 4 carbon atoms, and
w' is an integer 1 to 4,
with a compound of formula IV, $HOR_1'$   IV wherein
$R_1'$ is primary alkyl of 1 to 4 carbon atoms,
to produce a compound of formula Ia,

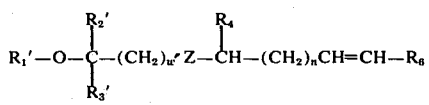   Ia wherein
$R_1'$, $R_2'$, $R_3'$, $R_4$, $R_6$, Z, w' and n are as defined above,
c. condensing a compound of formula V,

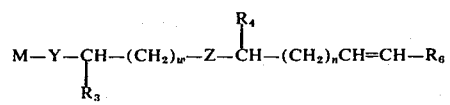   V wherein
$R_3$, $R_4$, $R_6$, Z, Y, w and n are as defined above, and
M is hydrogen, sodium or potassium,
with a compound of formula VI, $R_1''Q$   VI wherein
$R_1''$ is primary or secondary alkyl of 1 to 6 carbon atoms, primary or secondary alkenyl of 3 to 6 carbon atoms, primary or secondary alkynyl of 3 to 6 carbon atoms, cycloalkyl of 5 to 7 ring carbon atoms or cycloalkyl of 5 to 7 ring carbon atoms substituted by alkyl of 1 to 6 carbon atoms, and
Q is chlorine, bromine or tosyl,
in the presence of an acid acceptor when M of formula V is hydrogen,
to produce a compound of formula Ib,

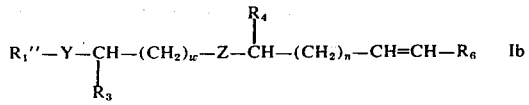   Ib wherein
$R_1''$, $R_3$, $R_4$, $R_6$, Z, Y, w and n are as defined above,
d. condensing a compound of formula VII,

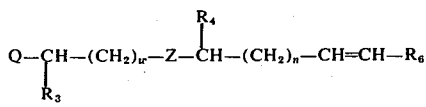   VII wherein
$R_3$, $R_4$, $R_6$, Z, Q, w and n are as defined above,
with a compound of formula VIII, $M - Y - R_1''$   VIII wherein
M, Y and $R_1''$ are as defined above, in the presence of an acid acceptor when M of formula VIII is hydrogen, to produce a compound of formula Ib, or
e. condensing a compound of formula IX,

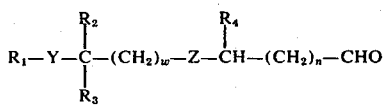   IX wherein
$R_1$, $R_2$, $R_3$, $R_4$, Y, Z, w and n are as defined above,
with an appropriate Wittig reagent, e.g. a compound of formula X,

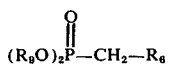   X wherein
$R_9$ is alkyl of 1 to 6 carbon atoms, preferably methyl or ethyl, and
$R_6$ is as defined above,
or a compound of formula XI,

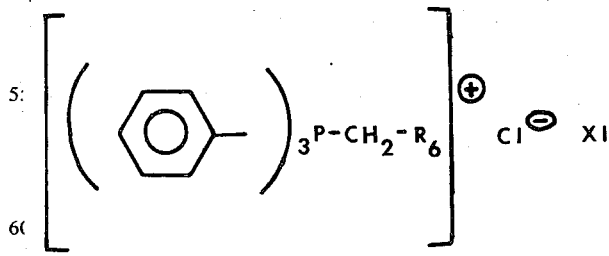   XI wherein
$R_6$ is as defined above,
preferably with a compound of formula X, under Wittig conditions, The process in accordance with variant a), above, may be effected as follows, viz:

In the case of dehydration of the compound of formula II, i.e. when in formula II, one of $X_1$ and $X_2$ is —OH, the reaction is conveniently effected in the presence of a dehydration agent such as an acid anhydride, e.g. phosphorous pentoxide, phthalic acid anhydride or acetic anhydride, conveniently in the presence of an acid, e.g. benzenesulphonic acid, dehydration agent such as an acid chloride, e.g. phosphorous oxychloride or thionylchloride in pyridine, or in a dehydration agent such as an acid or acid salt, e.g. oxalic acid, sulphuric acid, potassium hydrosulphate or, preferably, an aryl sulphonic acid, e.g. toluenesulphonic acid. The reaction mixture is preferably dissolved in a solvent such as a hydrocarbon solvent, e.g. benzene or xylene. Heating may be effected, depending on the nature of the dehydrating agent employed, and generally heating at the reflux temperature of the reaction mixture is convenient. The duration of the reaction will vary, e.g. between 10 minutes and 2½ hours. The final compound may be separated from the acid by extraction from the aqueous phase. Working up is effected in conventional manner [W. S. Emerson, Chem. Rev. 45, 347 (1949), General Methods; Houben-Weyl, Kohlenwasserstoffe, Vol V/1c part 3, p 15–70, Georg Thieme (1970)].

In a preferred mode of effecting process variant a), a compound of formula II, wherein one of $X_1$ and $X_2$ is —OH, is dehydrated in the presence of p-toluenesulphonic acid monohydrate, preferably present in less than an equivalent amount, by heating in benzene at the reflux temperature, e.g. for between 15 minutes and 2 hours, using a Dean-Stark trap.

When compounds of formula II having leaving groups other than —OH are employed, elimination of HX, X being a leaving group as defined above, may be effected in a suitable solvent such as a hydrocarbon, e.g. benzene or xylene, preferably with either base or acid catalysis, depending on the nature of the leaving group. Thus in the case when one of $X_1$ and $X_2$ is an alkyl or aryl sulphonate, the reaction is preferably effected in the presence of an acid catalyst, e.g. sulphuric acid or preferably an aryl sulphonic acid, preferably with heating. In the case when one of $X_1$ and $X_2$ is halogen, i.e. the reaction consists of dehydrohalogenation, the reaction is preferably effected in the presence of a basic catalyst, e.g. an alkali such as potassium hydroxide or an amine, preferably with heating.

Working up of the reaction mixture is effected in known manner.

The process in accordance with variant b), above, may be effected as follows, viz:

The selective condensation is preferably effected in the presence of a mercury (II) salt catalyst, especially mercury (II) acetate, with subsequent reduction of the resulting mercury complex, e.g. with sodium borohydride. Thus, conveniently, a compound of formula III is dissolved in an alcohol of formula IV in absolute form. To the solution so formed is added, conveniently dropwise, with stirring, at a reduced temperature, e.g. between 0° and 5°C, over a period of about 15 minutes, a solution of mercury (II) acetate, preferably in an excess of the alcohol of formula IV, in absolute form, as solvent. The reaction mixture is conveniently stirred at the reduced temperature for a period of, e.g. 30 minutes, and then potassium hydroxide, conveniently dissolved in an excess of the compound of formula IV, and sodium borohydride, are preferably added. The mixture is then conveniently stirred over an extended period, e.g. up to 14 hours, conveniently at room temperature. The resulting mercury is separated off and working up is effected in conventional manner, conveniently with the addition of water [H. C. Brown and P. Geoghegan, Jr., J. Am. Chem. Soc. 89, 1522 (1967)].

The process in accordance with variant c) above, may be effected as follows, viz:

A compound of formula V, preferably in sodium or potassium salt form, is preferably reacted with a compound of formula VI in an appropriate anhydrous solvent, e.g. a hydrocarbon solvent such as benzene, an ether solvent such as dioxane, 1,2-dimethoxyethane or diethyl glycol dimethyl ether, a ketone such as acetone, a nitrile such as acetonitrile or an acid amide such as dimethylformamide, in the presence of an acid acceptor, such as potassium tert. butylate, when M of formula V is hydrogen. The reaction temperature will, generally, vary between 0° and 100°C. The reaction period varies from between, e.g. 6 and 26 hours. When Y of formula V is sulphur, lower temperatures are generally employed, e.g. room temperature and below. When Y of formula V is oxygen, a higher temperature range is preferred, such as 50° to 100°C, e.g. 60°C.

In a preferred mode of effecting process variant c), the sodium or potassium salt of a compound of formula V is produced, in situ, at the beginning of the reaction from the free alcohol or thioalcohol form thereof, by reaction with, e.g. metallic sodium or a sodium hydride dispersion, preferably in an inert atmosphere, e.g. a nitrogen atmosphere.

Working up is effected in manner known per se.

The process in accordance with variant d) above, may be effected as follows, viz:

A compound of formula VIII, preferably in sodium or potassium salt form, is preferably reacted with a compound of formula VII in an appropriate anhydrous solvent, e.g. a hydrocarbon solvent such as benzene, an ether solvent such as dioxane, 1,2-dimethoxyethane or diethyl glycol dimethyl ether, a ketone such as acetone, a nitrile such as acetonitrile or an acid amide such as dimethylformamide, in the presence of an acid acceptor such as potassium tert. butylate, when M of formula VIII is hydrogen. The reaction temperature will vary, generally, between 0 to 100°C, higher temperatures being employed when Y of formula VIII is oxygen, lower temperatures being employed, e.g. below room temperature, when Y is sulphur. The reaction period will vary generally between, e.g. 5 and 24 hours.

Working up may be effected in conventional manner.

The process in accordance with variant e) may be effected as follows, viz:

A suspension of sodium methylate conveniently in slight excess is dissolved in a solvent such as absolute dimethylformamide or hexamethyl phosphoric triamide, and added whilst stirring and cooling, e.g. to 0°C, to a compound of formula IX. To this solution, a Wittig reagent, e.g. a compound of formula X, in an appropriate solvent, e.g. absolute dimethylformamide, is rapidly added, e.g. over a period of several minutes, with cooling. Stirring is continued, e.g. initially for about 1 hour, with cooling, e.g. to 0°C, and subsequently for e.g. 1½ hours, at room temperature. Preferably, the reaction is effected in an inert atmosphere, e.g. nitrogen.

Working up is effected in conventional manner, e.g. by addition of water and extraction of the compound with, e.g. hexane.

The starting materials of formula II are known or may be produced by the following processes, known per se, viz:

a'. by condensing a compound of formula XII,

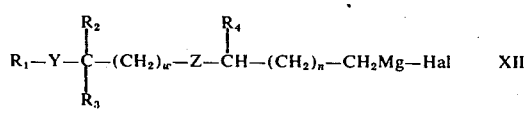

R$_1$—Y—C(R$_2$)(R$_3$)—(CH$_2$)$_w$—Z—CH(R$_4$)—(CH$_2$)$_n$—CH$_2$Mg—Hal    XII wherein
R$_1$, R$_2$, R$_3$, R$_4$, Y, Z, w and n are as defined above, and
Hal is chlorine, bromine or iodine,
with a compound of formula XIII,

R$_6$—CH=O    XIII wherein
R$_6$ is as defined above,
under Grignard conditions, to produce a compound of formula IIa,

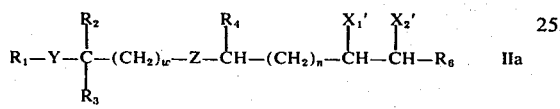

R$_1$—Y—C(R$_2$)(R$_3$)—(CH$_2$)$_w$—Z—CH(R$_4$)—(CH$_2$)$_n$—CH(X$_1'$)—CH(X$_2'$)—R$_6$    IIa wherein
R$_1$, R$_2$, R$_3$, R$_4$, R$_6$, Y, Z, w and n are as defined above,
X$_1'$ is hydrogen, and
X$_2'$ is —OH, or b'. by condensing a compound of formula XIV,

R$_6'$ CH$_2$ Mg — Hal    XIV wherein
Hal is as defined above, and
R$_6'$ is an aromatic group Ar$_1'$,

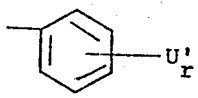

Ar$_1'$ or an aromatic group Ar$_2'$,

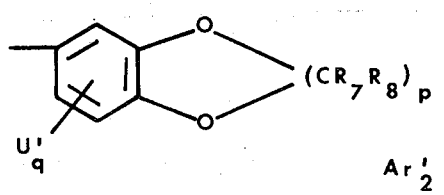

Ar$_2'$ wherein
r, q, p, R$_7$ and R$_8$ are as defined above, and
U' is alkyl of 1 to 6 carbon atoms, alkenyl of 2 to 6 carbon atoms, alkoxy of 1 to 6 carbon atoms, alkenyloxy of 3 to 6 carbon atoms, alkoxymethyl of 2 to 7 carbon atoms, alkylthio of 1 to 6 carbon atoms, or phenyl, with a compound of formula IX under Grignard conditions, to obtain a compound of formula IIb, R$_1$—Y—C(R$_2$)(R$_3$)—(CH$_2$)$_w$—Z—CH(R$_4$)—(CH$_2$)$_n$—CH(X$_1''$)—CH(X$_2''$)—R$_6'$    IIb wherein
R$_1$, R$_2$, R$_3$, R$_4$, R$_6'$, Y, Z, w and n are as defined above,
X$_1''$ is -OH, and
X$_2''$ is hydrogen.

The remaining compounds of formula II are either known or may be produced in manner known per se from the compounds of formulae IIa or IIb.

The compounds of formula III are either known or may be produced in manner known per se by elimination of HX,
wherein
X is as defined above,
from a compound of formula XV,

C(R$_2'$)(R$_3'$)=CH(CH$_2$)$_{w'-1}$—Z—CH(R$_4$)—(CH$_2$)$_n$CH(X$_1$)—CH(X$_2$)—R$_6$    XV wherein
R$_2'$, R$_3'$, R$_4$, R$_6$, Z, X$_1$, X$_2$, w' and n are as defined above,
in analogous manner to that described in relation to process variant a) for the production of final compounds of formula I.

The compounds of formulae, V, VI, VII, VIII and IX are either known or may be produced in accordance with known methods.

The compounds of formula X are known or may be produced, for example, by an Arbusow reaction of a phosphite of formula XVI, (R$_9$O)$_3$P    XVI wherein
R$_9$ is as defined above,
with a compound of formula XVII R$_6$CH$_2$—Hal    XVII wherein
R$_6$ and Hal are as defined above.

When Hal of formula XVII is chlorine, the reaction with the phosphite is preferably effected with the addition of one equivalent of lithium bromide.

The halogen starting compounds required for the production of the Grignard compounds of formula XII are known or may be produced in accordance with known methods, e.g.:

a''. by reacting an alcohol of formula XVIII

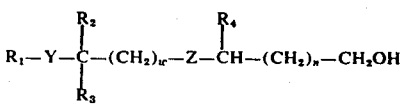

R$_1$—Y—C(R$_2$)(R$_3$)—(CH$_2$)$_w$—Z—CH(R$_4$)—(CH$_2$)$_n$—CH$_2$OH    XVIII wherein
R$_1$, R$_2$, R$_3$, R$_4$, Y, Z, w and n are as defined above, with a halogenating agent under the usual conditions to avoid ether cleavage [Houben-Weyl, Methoden der organischen Chemie, Vol V/4, pages 361–411 (1960), and Vol V/3 pages 862 et seq (1962), Georg Thieme], b''. by reacting a compound of formula XIX,

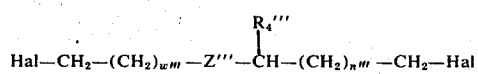   XIX wherein
Hal is as defined above, and
$w'''$, $Z'''$, $R_4'''$ and $n'''$ have the same significances as $w$, $Z$, $R_4$ and $n$ respectively, with the proviso that the portion

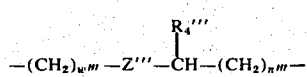

is symmetrical, e.g. when $R_4'''$ is H, and $Z'''$ is —$CH_2$—,
with a compound of formula VIII, in the presence of an acid acceptor when M of formula VIII is hydrogen, to produce a compound of formula XIIa,

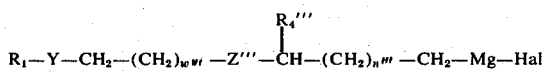

wherein
$R_1$, $R_4'''$, Y, $Z'''$, $w'''$, $n'''$ and Hal are as defined above, or c'') reacting a compound of formula XX,

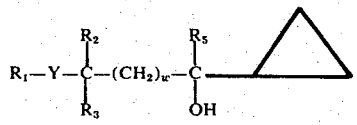   XX wherein
$R_1$, $R_2$, $R_3$, $R_5$, Y and $w$ are as defined above, with 48 % hydrobromic acid, to obtain a compound of formula XIIb,

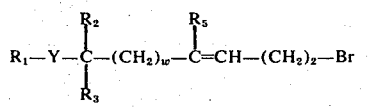   XIIb wherein
$R_1$, $R_2$, $R_3$, $R_5$, Y and $w$ are as defined above,
and when desired, replacing the terminal bromine atom by chlorine or iodine.

The alcohols of formula XVIII are either known or may be produced in manner known per se, e.g. a'''. by reacting a compound of formula XXI,

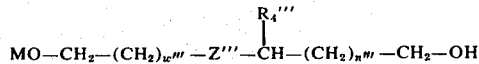

wherein
M, $Z'''$, $R_4'''$, $w'''$ and $n'''$ are as defined above, with a compound of formula VI in the presence of an acid acceptor when M of formula XXI is hydrogen, to produce a compound of formula XVIIIa

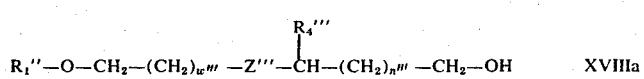   XVIIIa wherein
$R_1''$, $R_4'''$, $Z'''$, $w'''$ and $n'''$ are as defined above, or b'''. by hydrogenating a compound of formula XXII,

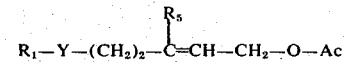   XXII wherein
$R_1$, $R_5$ and Y are as defined above, and
Ac is a hydroxy function protecting group, e.g. acetyl,
and subsequently removing the protecting group to produce a compound of formula XVIIIb, XIIa

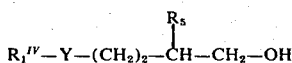   XVIIIb wherein
$R_5$ and Y are as defined above, and
$R_1^{IV}$ is alkyl of 1 to 6 carbon atoms, cycloalkyl of 5 to 7 carbon atoms or cycloalkyl of 5 to 7 ring carbon atoms substituted by alkyl of 1 to 6 carbon atoms.

The compounds of formula XXII are either known or may be produced, e.g., by addition of a compound of formula XXIII

   $R_1$—O—$CH_2$—Cl   XXIII wherein
$R_1$ is as defined above,
to a compound of formula XXIV,

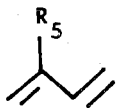   XXIV

XXI wherein
R₅ is as defined above,
in the presence of an addition catalyst such as zinc chloride, and exchanging the terminal chlorine atom of the resulting compound of formula XXVI,

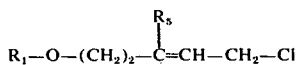    XXVI wherein
R₁ and R₅ are as defined above,
by a protected hydroxyl function, e.g., by reaction with sodium or potassium acetate, to produce a compound of formula XXIIa,

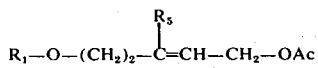    XXIIa wherein
R₁, R₅ and Ac are as defined above.
The compounds of formula XXI may be produced in manner known per se, e.g., by reacting a compound of formula XXVII,

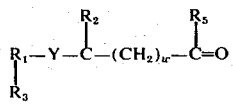    XXVII wherein
R₁, R₂, R₃, R₅, Y and w are as defined above, with a compound of formula XXVIII,

    XXVIII wherein
Hal' is chlorine or bromine,
and subsequently hydrolysing the resulting magnesium compound.

Insofar as the production of starting materials has not been described, these are either known or may be produced in accordance with processes known per se or in analogous manner to the processes described herein or to the processes known per se.

The compounds of formula I are, in general, colourless oils. They may be prepared, and characterized in conventional manner, e.g. by distillation or chromatography.

The compounds of formula I possess insecticidal and acaricidal properties in the sense that they exhibit an inhibiting effect on the development of insects and acarids from one development stage thereof to the next, to result either in death, reduced oviposition or inhibition of copulation and thereby to a reduced insect or acarid population. The above-mentioned effect of the compounds of formula I is indicated by the following tests, viz:

TEST 1

Insecticidal effect on Dysdercus fasciatus larvae (Egyptian cotton worm)

Filter paper is impregnated (0.1 mg/cm²) with a solution of the active agent of formula I, e.g.,
1-(6-Isopropoxy-4-methyl-1-hexenyl)-3,4-methylenedioxybenzene,
1-(7-Isopropoxy-1-heptenyl)-3,4-methylenedioxybenzene,
1-(6-Isopropoxy-1-hexenyl)-3,4-methylenedioxybenzene,
1-(5-Isopentyloxy-1-pentenyl)-3,4-methylenedioxybenzene,
1-(8-Methoxy-4,8-dimethyl-1-nonenyl)-3,4-methylenedioxybenzene,
1-(7-Isopropoxy-5-methyl-1,4-heptadienyl)-3,4-methylenedioxybenzene,
1-(6-sec-Butoxy-4-methyl-1-hexenyl)-3,4-methylenedioxybenzene,
1-(7-sec-Butoxy-1-heptenyl)-3,4-methylenedioxybenzene,
1-(8-Methoxy-4,8-dimethyl-1-nonenyl)-4-nitrobenzene,
1-Chloro-4-(8-methoxy-4,8-dimethyl-1-nonenyl)benzene and
1-(7-Isopropoxy-1-heptenyl)-4-nitrobenzene.

A box made from polystyrene (200 × 100 × 85 mm) is coated with the filter paper treated in this way. A folded filter paper, which is also impregnated, is covered with about 30 Dysdercus larvae of the 4th larval stage and placed into the box. Pounded cotton seeds, as food, and a drinking vessel are placed into the box. The rate of development is determined after 10 days. The rate of development of the Dysdercus larvae into adults was found to be substantially reduced or inhibited.

TEST 2

Insecticidal effect on the development of Prodenia littura larvae (cotton stainer) into adults Filter paper is impregnated (0.1 mg/cm²) with a solution of the active agent of formula I, e.g.
1-(6-Isopropoxy-4-methyl-1-hexenyl)-3,4-methylenedioxybenzene,
1-(7-Isopropoxy-1-heptenyl)-3,4-methylenedioxybenzene,
1-(7-Isopentyloxy-1-heptenyl)-3,4-methylenedioxybenzene,
1-(6-Isopropoxy-1-hexenyl)-3,4-methylenedioxybenzene,
1-(8-Methoxy-4,8-dimethyl-1-nonenyl)-3,4-methylenedioxybenzene,
1-(7-Isopropoxy-5-methyl-1,4-heptadienyl)-3,4-methylenedioxybenzene,
1-(6-sec-Butoxy-4-methyl-1-hexenyl)-3,4-methylenedioxybenzene and
1-(7-sec-Butoxy-1-heptenyl)-3,4-methylenedioxybenzene.

Compartments of a plastic box are coated with the filter paper treated in this way. One Prodenia caterpillar is placed into each compartment and a piece of artificial medium is given as food. The number of the normally developed adults is determined after 21 days. The rate of development of the larvae into adults is found to be substantially reduced or inhibited.

TEST 3

Insecticidal effect on the development of Tenebrio molitor larvae (flour beetle) into adults The compounds of formula I, e.g.
1-(6-Isopropoxy-4-methyl-1-hexenyl)-3,4-methylenedioxybenzene,
1-(7-Isopropoxy-1-heptenyl)-3,4-methylenedioxybenzene,
1-(7-Isopentyloxy-1-heptenyl)-3,4-methylenedioxybenzene,
1-(8-Methoxy-4,8-dimethyl-1-nonenyl)-3,4-methylenedioxybenzene,
1-(7-Isopropoxy-5-methyl-1,4-heptadienyl)-3,4-methylenedioxybenzene,
1-(6-sec-Butoxy-4-methyl-1-hexenyl)-3,4-methylenedioxybenzene,
1-(7-sec-Butoxy-1-heptenyl)-3,4-methylenedioxybenzene,
1-(8-Methoxy-4,8-dimethyl-1-nonenyl)-4-nitrobenzene,
1-Chloro-4-(8-methoxy-4,8-dimethyl-1-nonenyl)benzene and
1-(7-Isopropoxy-1-heptenyl)-4-nitrobenzene,
are used at concentrations of 1 % of active agent in acetone solution. 2 μ l of the solution, which corresponds to 20 micrograms of active agent, are applied to the abdominal side of the last three body segments of young caterpillars (not older than 18 hours) by means of a 1-microliter bulb pipette. 10 larvae are used for each test. The treated larvae are kept at 28° in plastic cups. The normally developed adults are counted after 10 to 12 days. The rate of development of larvae is found to be substantially reduced or inhibited.

TEST 4

Acaricidal contact effect in Tetranychus urticae (red spider mite)

One day before treatment, 10 adult females of Tetranychus urticae are placed by means of a fine brush between two rings (diameter: 3 cm) of caterpillar glue which are applied to a leaf of a cotton plant. The cotton leaves are sprayed to run off by means of a sprayer with a liquor containing 0.1 % of active agent, e.g.
1-(6-sec-Butoxy-4-methyl-1-hexenyl)-3,4-methylenedioxybenzene and
1-(7-sec-Butoxy-1-heptenyl)-3,4-methylenedioxybenzene.
The liquor is allowed to dry and then the plants are kept at room temperature and in light. The dead and live insects are counted 6 days after the treatment. The ratio between the treated and an untreated population indicates the effect. The results indicate a substantial reduction or inhibition of oviposition.

Aside from their insecticidal and acaricidal effects, the compounds of formula I exhibit only low mammalian toxicity.

The compounds of formula I are therefore useful as insecticides and acaricides, particularly in applications where low mammalian toxicity is desirable, e.g. in plant protection.

For the abovementioned uses, the amount applied to a locus to be treated will of course vary depending on the compound employed, the mode of application, ambient conditions, and the insects or acarids to be combated. However, with regard to plant protection, satisfactory results are indicated when applied to a plant locus in an amount of between 1 and 4 kg/hectare, the application being repeated as required.

The compounds may be applied to the locus with conventional applicator equipment and by conventional methods e.g. strewing, spraying and dusting.

Compositions may comprise a compound of formula I in admixture with insecticidal or acaricidal carriers, diluents and/or adjuvants in solid or liquid form, e.g. spraying and dusting powders, granulates, liquid sprays and aerosols.

Solid forms may include diluents and carriers, such as diatomaceous earth, bentonite and pumice. Adjuvants, e.g. surfactants, such as wetting and dispersing agents, and adhesive agents, e.g. cellulose derivatives, may also be included in the case of wettable powders to be applied as a water suspension. Granulates are produced by coating or impregnating granular carrier materials, such as pumice, limestone, attapulgite and koalinite, with the compounds.

Liquid forms may include non-phytotoxic diluents and carriers such as alcohols, aliphatic and aromatic hydrocarbons, e.g. xylene, alkyl naphthalenes and other petroleum distillates. Adjuvants such as surface active agents, e.g. wetting and emulsifying agents such as polyglycol ethers formed by the reaction of an alkylene oxide with high molecular weight alcohols, mercaptans or alkyl phenols, e.g. isooctylphenyloctaglycol ether or isooctylphenyldecaglycol ether, may be included in emulsion concentrate forms. Appropriate organic solvents, e.g. ketones, aromatic optionally halogenated hydrocarbons and mineral oils may also be included as solvent aids.

Aside from the abovementioned carriers, diluents and adjuvants, adjuvants such U.V. stabilizing agents, antioxidants, desactivators (for solid forms with carriers having an active surface), agents for improving adhesiveness to surfaces treated, anticorrosives, defoaming agents, evaporation reducing agents, and pigments may also be included.

Concentrate forms of composition generally contain between 2 and 90 %, preferably between 5 and 50 %, by weight of active compound.

Application forms of compositions generally contain between 0.01 % and 10 % and preferably between 0.01 and 0.4 %, e.g. between 0.01 and 0.1 % by weight of active compound.

Examples of concentrate forms of composition will now be described.

a. Emulsifiable concentrate 25 parts by weight of a compound of formula I are mixed with 25 parts by weight of isooctylphenyldecaglycol ether and 50 parts by weight of xylene, whereby a clear solution is obtained which may be readily emulsified in water. The concentrate may be diluted with water to the desired concentration.

b. Emulsifiable concentrate 25 parts by weight of a compound of formula I are mixed with 30 parts by weight of isooctylphenyloctaglycol ether and 45 parts by weight of a of a petroleum fraction having a B.P. of 210°–280° ($D_{20}$ : 0.92). The concentrate may be diluted with water to the desired concentration.

c. Emulsifiable concentrate 50 parts by weight of a compound of formula I are mixed with 50 parts by weight of isooctylphenyloctaglycol ether. A clear concentrate is obtained which may be readily emulsified with water and which may be diluted with water to the desired concentration.

A preferred group of final compounds are the compounds of formula I,
wherein
R₁ is alkyl of 1 to 6 carbon atoms, especially branched or secondary alkyl of 3 to 6 carbon atoms,
R₂, R₃ and R₄ are, independently, hydrogen or or alkyl of 1 to 3 carbon atoms,
Z is a divalent group —CR₅=CH—, —CH=CR₅— or —CHR₅, especially —CHR₅—
wherein
R₅ is hydrogen or alkyl of 1 to 3 carbon atoms,
Y is oxygen or sulphur, especially oxygen,
w and n are, independently zero or an integer 1 to 4 and
R₆ is an aromatic radical Ar₁,
wherein
U is alkyl of 1 to 4 carbon atoms, alkoxy of 1 to 4 carbon atoms, alkylthio of 1 to 4 carbon atoms, alkoxycarbonyl of 2 to 6 carbon atoms, nitro, chloro or bromo, especially alkyl of 1 to 4 carbon atoms, alkoxy and alkylthio of 1 to 4 carbon atoms, nitro or chlorine, and
r is 1 or 2, especially such compounds when one or both of R₄ and R₅ are straight chain alkyl of 1 to 3 carbon atoms.

Another preferred group of final compounds are the compounds of formula I,
wherein
R₁ is alkyl of 1 to 6 carbon atoms, especially branched or secondary alkyl of 3 to 6 carbon atoms,
R₂, R₃ and R₄ are, independently, hydrogen or alkyl of 1 to 3 carbon atoms,
Z is a divalent group —CR₅=CH—, —CH=CR₅— or —CHR₅—, especially —CHR₅—,
wherein
R₅ is hydrogen or alkyl of 1 to 3 carbon atoms,
Y is oxygen or sulphur, especially oxygen,
w and n are, independently zero or an integer 1 to 4, and
R₆ is an aromatic radical Ar₂,
wherein
R₇ and R₈ are each hydrogen,
p is 1
q is 0, 1 or 2, especially 0, and
U is alkyl of 1 to 4 carbon atoms, alkoxy of 1 to 4 carbon atoms, alkylthio of 1 to 4 carbon atoms, alkoxycarbonyl of 2 to 6 carbon atoms, nitro, chlorine or bromine, especially alkyl, alkoxy and alkylthio of 1 to 4 carbon atoms, nitro or chlorine, especially such compounds when one or both of R₄ and R₅ are straight chain alkyl of 1 to 3 carbon atoms.

Examples of the process of this invention will now be described. Where temperature is referred to, this is in °C.

I. FINAL COMPOUNDS

EXAMPLE 1

1-(6-Isopropoxy-4-methyl-1-hexenyl)-3,4-methylenedioxybenzene 6.50 g (0.022 mol) of 1-(1-hydroxy-6-isopropoxy-4-methyl-hexyl)-3,4-methylenedioxybenzene are boiled at reflux together with 0.30 g (0.0016 mol) of p-toluenesulphonic acid monohydrate in 500 cc of benzene over the course of 2 hours and using a Dean-Stark trap. After cooling to room temperature, the benzene solution is washed with saturated sodium bicarbonate solution, water and saturated sodium chloride solution, dried with sodium sulphate and evaporated in a vacuum. After chromatography of the residue on silica gel wth hexane/ethyl acetate (98:2), pure 1-(6-isopropoxy-4-methyl-1-hexenyl)-3,4-methylenedioxybenzene is obtained as a colourless oil. $n_D^{20}$ = 1.5258.

| Analysis: | $C_{17}H_{24}O_3$ | | Molecular weight: 276.4 | |
|---|---|---|---|---|
| Calc. | C 73.9 % | H 8.8 % | O | 17.4 % |
| Found | 73.8 % | 8.6 % | | 17.3 % |

EXAMPLE 2

1-(5-Isopentyloxy-1-pentenyl)-3,4-methylenedioxybenzene 0.07 g (0.37 millimol) of p-toluenesulphonic acid-monohydrate are added to 2.2g (0.0075 mol) of 1-(1-hydroxy-5-isopentyloxy-pentyl)-3,4-methylenedioxybenzene, dissolved in 150 cc of benzene. The solution is rapidly heated to boiling temperature and boiled at reflux over the course of 20 minutes and using a Dean-Stark-trap. After cooling, the benzene solution is extracted with saturated sodium bicarbonate solution, subsequently with water and saturated sodium chloride solution and dried with sodium sulphate. The solution is evaporated and the residue chromatographed on silica gel with hexane/ethyl acetate (97:3), whereupon the 1-(5-isopentyloxy-1-pentenyl)-3,4-methylenedioxybenzene is obtained as a pure, colourless oil. $n_D^{20}$ = 1.5248

| Analysis: | $C_{14}H_{24}O_3$ | | Molecular weigh 276.4 | |
|---|---|---|---|---|
| Calc. | C 73.9 % | H 8.7 % | O | 17.4 % |
| Found | 73.8 % | 8.8 % | | 17.7 % |

EXAMPLE 3

1-(7-Isopentyloxy-1-heptenyl)-3,4-methylenedioxybenzene

Replacing 1-(1-hydroxy-5-isopentyloxy-pentyl)-3,4-methylenedioxybenzene by 1-(1-hydroxy-7-isopentyloxyheptyl)-3,4-methylenedioxybenzene, the above compound is produced in analogous manner to that described in Example 2. $n_D^{20}$ = 1.5220.

| Analysis: | $C_{19}H_{28}O_3$ | | Molecular weight: 304.4 | |
|---|---|---|---|---|
| Calc. | C 75.0 % | H 9.3 % | O | 15.8 % |
| Found | 75.0 % | 9.6 % | | 15.9 % |

EXAMPLE 4

1-(7-Isopropoxy-1-heptenyl)-3,4-methylenedioxybenzene

The above compound is produced in analogous manner to that described in Example 2, but replacing 1-(1-hydroxy-5-isopentyloxy-pentyl)-3,4-methylenedioxybenzene by 1-(1-hydroxy-7isopropoxy-heptyl)-3,4-methylenedioxybenzene. $n_D^{20}$ = 1.5268.

| Analysis: | $C_{17}H_{24}O_3$ | | Molecular weight: 276.4 | |
|---|---|---|---|---|
| Calc. | C 73.9 % | H 8.8 % | O | 17.4 % |

-continued

| Found | 73.9 % | 8.7 % | 18.2 % |

EXAMPLE 5

1-(6-Isopropoxy-1-hexenyl)-3,4-methylenedioxybenzene

The above compound is produced in analogous manner to that described in Example 2, but replacing 1-(1-hydroxy-5-isopentyloxy-pentyl)-3,4-methylenedioxybenzene by 1-(1-hydroxy-6-isopropoxy-hexyl)-3,4-methylenedioxybenzene. $n_D^{20} = 1.5316$

| Analysis: | $C_{16}H_{22}O_3$ | Molecular weight: 262.3 | |
|---|---|---|---|
| Calc. | C 73.3 % | H 8.5 % | O 18.3 % |
| Found | 72.8 % | 8.6 % | 18.1 % |

EXAMPLE 6

1-(7-Isopropoxy-5-methyl-1,4-heptadienyl)-3,4-methylendioxybenzene

The above compound is produced in manner analogous to that described in Example 2, but replacing 1-(1-hydroxy-5-isopentyloxy-pentyl)-3,4-methylenedioxybenzene by 1-(1-hydroxy-7-isopropoxy-5-methyl-4-heptenyl)-3,4-methylenedioxybenzene. $n_D^{20} = 1.5398$.

| Analysis: | $C_{18}H_{24}O_3$ | Molecular weight: 288.4 | |
|---|---|---|---|
| Calc. | C 75.0 % | H 8.4 % | O 16.6 % |
| Found | 75.0 % | 8.3 % | 16.1 % |

EXAMPLE 7

1-(6-sec-Butoxy-4-methyl-1-hexenyl)-3,4-methylenedioxybenzene

The above compound is produced in analogous manner to that described in Example 2, but replacing 1-(1-hydroxy-5-isopentyloxy-pentyl)-3,4th-methylenedioxybenzene by 1-(1-hydroxy-6-sec-butoxy-4-methyl-hexyl)-3,4-methylenedioxybenzene. $n_D^{20} = 1.5261$

| Analysis: | $C_{18}H_{26}O_3$ | Molecular weight: 290.4 | |
|---|---|---|---|
| Calc. | C 74.4 % | H 9.0 % | O 16.5 % |
| Found | 73.4 % | 8.9 % | 17.1 % |

EXAMPLE 8

1-(7-sec-Butoxy-1-heptenyl)-3,4-methylenedioxybenzene

The above compound is produced in analogous manner to that described in Example 2, but replacing 1-(1-hydroxy-5-isopentyloxy-pentyl)-3,4-methylenedioxybenzene by 1-(1-hydroxy-7-sec-butoxcy-heptyl)-3,4-methylenedioxybenzene. $n_D^{20} = 1.5236$

| Analysis: | $C_{18}H_{26}O_3$ | Molecular weight: 290.4 | |
|---|---|---|---|
| Calc. | C 74.4 % | H 9.0 % | O 16.5 % |
| Found | 74.1 % | 8.9 % | 16.9 % |

EXAMPLE 9

1-(8-Methoxy-4,8-dimethyl-1-nonenyl)-3,4-methylenedioxybenzene

A solution of 0.862 g (2.93 millimols) of mercury diacetate in 20 cc of absolute methanol is added dropwise, whilst stirring, at 0°–5°C, over the course of 15 minutes, to 0.50 g (1.84 millimols) of 1-(4,8-dimethyl-1,7-nonadienyl)-3,4-methylenedioxybenzene in 10 cc of absolute methanol. The mixture is stirred for a further 30 minutes at 0°–5°C. 0.72 g (12.8 millimols) of potassium hydroxide in 10 cc of methanol, followed by 0.053 g (1.40 millimols) of sodium borohydride, are subsequently added. The mixture is stirred at room temperature over night, the solution is decanted off from the resulting mercury and 50 cc of water are added. The mixture is concentrated by evaporation to 40 cc in a vacuum. The residue is extracted with ether, the extract is washed with water and saturated sodium chloride solution, dried over sodium sulphate and evaporated. After chromatography of the residue on silica gel with hexane/ethyl acetate (98:2), pure 1-(8-methoxy-4,8-dimethyl-1-nonenyl)-3,4-methylenedioxybenzene is obtained as a colourless oil apart from a small amount of starting material. $n_D^{20} = 1.5288$.

| Analysis: | $C_{19}H_{28}O_3$ | Molecular weight: 304.4 | |
|---|---|---|---|
| Calc. | C 75.0 % | H 9.3 % | O 15.7 % |
| Found | 74.8 % | 9.3 % | 15.8 % |

EXAMPLE 10

1-(8-Methoxy-4,8-dimethyl-1-nonenyl)-4-nitrobenzene

A mixture consisting of 5.4 g (0.025 mol) of p-nitrobenzyl bromide and 4.15 g (0.025 mol) of triethyl phosphite is stirred at 90°, over the course of 1 hour and under nitrogen. The resulting ethyl bromide is distilled off from the reaction vessel. The obtained solution is then evacuated and stirred at a bath temperature of 110° for one further hour in a water jet vacuum. A suspension consisting of 1.68 g (0.030 mol) of sodium methylate and 10 cc of absolute dimethylformamide is carefully added at 0° to the residue. 4.65 g (0.025 mol) of 7-methoxy-3,7-dimethyloctanol in a small amount of dimethylformamide are subsequently added over the course of 5 minutes to the red reaction mixture which is stirred at 0° for 1 hour and at room temperature for 90 minutes. The ruby-coloured solution gradually turns dark brown. 60 cc of water are added and the reaction mixture is extracted with hexane. The extracts are washed with water and saturated sodium chloride solution, dried over magnesium sulphate and evaporated at 40°/20 mm Hg. After chromatography of the residue on silica gel with hexane/ethyl acetate (97:3) and (94:6), pure 1-(8-methoxy-4,8-dimethyl-1-nonenyl)-4-nitrobenzene is obtained as a slightly yellow oil. $n_D^{20} = 1.5473$

| Analysis: | $C_{18}H_{27}NO_3$ | Molecular weight: 305.4 | | |
|---|---|---|---|---|
| Calc. | C 70.8 % | H 8.9 % | N 4.6 % | O 15.7 % |
| Found | 71.1 % | 9.0 % | 4.6 % | 15.9 % |

EXAMPLE 11

1-Chloro-4-(8-methoxy-4,8-dimethyl-1-nonenyl)-benzene

The above compound is produced in analogous manner to that described in Example 10, but using a mixture of p-chlorobenzyl chloride and 1 equivalent of lithium bromide in the place of p-nitrobenzyl bromide. $n_D^{20} = 1.5243$

| Analysis: | $C_{18}H_{27}ClO$ | Molecular weight: 294.9 | |
|---|---|---|---|
| Calc. | C 73.3 % | H 9.2 % | Cl 12.0 % |
| Found | 73.2 % | 9.0 % | 12.2 % |
| | O 5.4 % | | |
| | 5.8 % | | |

EXAMPLE 12

1-(7-Isopropoxy-1-heptenyl)-4-nitrobenzene

The above compound is produced in analogous manner to that described in Example 10, but using 6-isopropoxyhexanal in the place of 7-methoxy-3,7-dimethyloctanol. $n_D^{20} = 1.5490$

| Analysis: | $C_{16}H_{23}NO_3$ | Molecular weight: 277.4 | | |
|---|---|---|---|---|
| Calc. | C 69.3 % | H 8.4 % | N 5.1 % | O 17.3 % |
| Found | 68.9 % | 8.3 % | 5.0 % | 17.7 % |

II. STARTING MATERIALS

Compounds of formula II

The alcohols of general formula II, used as starting material, may be produced in accordance with the following Examples 13 to 20:

EXAMPLE 13

1-(1-Hydroxy-6-isopropoxy-4-methyl-hexyl)-3,4-methylenedioxybenzene

To 10.1 g (0.067 mol) of piperonal in 100 cc of absolute ether is added whilst stirring, at −10°C, over the course of 45 minutes, the ether solution of the Grignard reagent, produced from 1.61 g (0.067 mol) of magnesium, a small grain of iodine, and 14.9 g (0.067 mol) of 1-bromo-5-isopropoxy-3-methylpentane in 180 cc of absolute ether. The mixture is subsequently stirred at room temperature for 1 hour, saturated ammonium chloride solution is added and the product is extracted with ether. The ether extracts are washed with water and saturated sodium chloride solution, dried with sodium sulphate and freed from the ether in a vacuum. After chromatography of the residue on silica gel with hexane/ethyl acetate (9:1), 1-(1-hydroxy-6-isopropoxy-4-methyl-hexyl)-3,4-methylenedioxybenzene is obtained as a colourless oil.

| Analysis: | $C_{17}H_{26}O_4$ | Molecular weight: 294.4 | |
|---|---|---|---|
| Calc. | C 69.4 % | H 8.9 % | O 21.7 % |
| Found | 70.4 % | 9.1 % | 21.6 % |

EXAMPLE 14

1-(1-Hydroxy-5-isopentyloxy-pentyl)-3,4-methylenedioxybenzene

A solution of 4.37 g (0.029 mol) of piperonal in 15 cc of absolute ether is added dropwise, whilst stirring, at 0°-5°C, over the course of 20 minutes, to a solution of the Grignard reagent, produced from 0.70 g (0.029 mol) of magnesium and 6.50 g (0.029 mol) of 1-bromo-4-isopentyloxy-butane in 25 cc of ether. The mixture is stirred at 20°-25°C for 18 hours. 10 cc of saturated ammonium chloride solution are subsequently added and the reaction mixture is extracted with ether. The ether extracts are washed with saturated sodium chloride solution, dried with sodium sulphate and evaporated. The residue is purified by chromatography on silica gel with hexane/ethyl acetate (9:1), whereby 1-(1-hydroxy-5-isopentyloxy-pentyl)-3,4-methylenedioxybenzene is obtained as a colourless oil. $n_D^{20} = 1.5064$

| Analysis: | $C_{17}H_{26}O_4$ | Molecular weight: 280.4 |
|---|---|---|
| Calc. | C 69.4 % | H 8.9 % |
| Found | 69.7 % | 9.0 % |

EXAMPLE 15

1-(1-Hydroxy-7-isopentyloxy-heptyl)-3,4-methylenedioxybenzene

The above compound is produced in analogous manner to that described in Example 14, but using 1-bromo-6-isopentyloxy-hexane in the place of 1-bromo-4-isopentyloxy-butane.

| Analysis: | $C_{19}H_{30}O_4$ | Molecular weight: 322.4 |
|---|---|---|
| Calc. | C 70.8 % | H 9.4 % |
| Found | 70.3 % | 9.3 % |

EXAMPLE 16

1-(1-Hydroxy-7-isopropoxy-heptyl)-3,4-methylenedioxybenzene

The above compound is produced in analogous manner to that described in Example 14, but using 1-bromo-6-isopropoxy-hexane in the place of 1-bromo-4-isopentyloxy-butane. $n_D^{20} = 1.5002$.

| Analysis: | $C_{17}H_{26}O_4$ | Molecular weight: 294.4 | |
|---|---|---|---|
| Calc. | C 69.4 % | H 8.9 % | O 21.7 % |
| Found | 68.9 % | 8.9 % | 21.2 % |

EXAMPLE 17

1-(1-Hydroxy-6-sec-butoxy-4-methyl-hexyl)-3,4-methylenedioxybenzene

The above compound is produced in analogous manner to that described in Example 14, but using 1-bromo-5-sec-butoxy-3-methyl-pentane in the place of 1-bromo-4-isopentyloxy-butane. $nD^{20} = 1.5075$

| Analysis: | $C_{18}H_{28}O_4$ | Molecular weight: 308.4 |
|---|---|---|
| Calc. | C 70.1 % | H 9.2 % |

EXAMPLE 18

1-(1-Hydroxy-7-sec-butoxy-heptyl)-3,4-methylenedioxybenzene

The above compound is produced in analogous manner to that described in Example 14, but using 1-bromo-6-sec-butoxyhexane in the place of 1-bromo-4-isopentyloxy-butane.

| Analysis: | $C_{18}H_{28}O_4$ | Molecular weight: | 308.4 |
|---|---|---|---|
| Calc. | C 70.1 % | H 9.2 % | O 20.8 % |
| Found | 69.9 % | 9.3 % | 20.3 % |

EXAMPLE 19

1-(1-Hydroxy-7-isopropoxy-5-methyl-4-heptenyl)-3,4-methylenedioxybenzene

The above compound is produced in analogous manner to that described in Example 14, but using 1-bromo-6-isopropoxy-4-methyl-3-hexene in the place of 1-bromo-4-isopentyloxy-butane.

| Analysis: | $C_{18}H_{28}O_4$ | Molecular weight: 306.4 |
|---|---|---|
| Calc. | C 70.6 % | H 8.6 % |
| Found | 70.0 % | 8.5 % |

EXAMPLE 20

1-(1-Hydroxy-6-isopropoxy-hexyl)-3,4-methylenedioxybenzene

A Grignard reagent is produced in 30 cc of ether from 0.407 g (0.017 mol) of magnesium and 3.55 g (0.017 mol) of 1-bromo-5-isopropoxy-pentane. A solution of 1.19 g (0.017 mol) of piperonal in 20 cc of absolute ether is added at 0°–5°C over the course of 15 minutes. The mixture is stirred at 20°–25° over the course of 4 hours and 20 cc of 2N sulphuric acid are subsequently added. The reaction mixture is extracted with ether, the ether extracts are washed with saturated sodium chloride solution, dried with sodium sulphate and evaporated. The residue is chromatographed on silica gel with hexane/ethyl acetate (95:5), whereupon the 1-(1-hydroxy-6-isopropoxy-hexyl)-3,4-methylenedioxybenzene is obtained as a pure, colourless oil.

| Analysis: | $C_{16}H_{24}O_4$ | Molecular weight: 280.4 |
|---|---|---|
| Calc. | C 68.5 % | H 8.6 % |
| Found | 67.9 % | 8.6 % |

Compounds of formula III

The compounds of formula III may, for example, be produced in accordance with Example 21:

EXAMPLE 21

1-(4,8-Dimethyl-1,7-nonadienyl)-3,4-methylenedioxybenzene

The above compound is produced in analogous manner to that described in Example 2, but using 1-(1-hydroxy-4,8-dimethyl-7-nonenyl)-3,4-methylenedioxybenzene in the plate of 1-(1-hydroxy-4-isopentyloxybutyl)-3,4-methylenedioxybenzene. $n_D^{20}$= 1.5426.

| Analysis: | $C_{18}H_{24}O_2$ | Molecular weight: | 272.4 |
|---|---|---|---|
| Calc. | C 79.5 % | H 8.9 % | O 11.7 % |
| Found | 78.9 % | 8.7 % | 11.0 % |

Compounds of formula XV

The compounds of general formula XV, suitable for the production of the compounds of general formula III, may, for example, be produced in accordance with Example 22:

EXAMPLE 22

1-(1-Hydroxy-4,8-dimethyl-7-nonenyl)-3,4-methylenedioxybenzene

The above compound is produced in analogous manner to that described in Example 14, but using Citronelly bromide in the place of 1-bromo-4-isopentyloxy-butane.

| Analysis: | $C_{18}H_{26}O_3$ | Molecular weight: | 290.4 |
|---|---|---|---|
| Calc. | C 74.5 % | H 9.0 % | O 16.5 % |
| Found | 74.8 % | 8.8 % | 15.9 % |

Halogen starting materials for Grignard compounds of formula XII

The halogen compounds, required for the production of the Grignard compounds of general formula XII, may, for example, be produced in accordance with Examples 23–30:

EXAMPLE 23

1-Bromo-4-isopentyloxy-butane

To a mixture of 6.4 g (0.4 mol) of 4-isopentyloxy-butanol and 0.32 g (0.004 mol) of pyridine in 40 ml of chloroform are added over a period of 15 minutes with stirring at 0°, 1.42 ml (0.015 mol) of phosphorus tribromide. The mixture is stirred for a period of one hour at 20° and then for 20 hours at 60°C. After cooling to room temperature, the reaction mixture is poured into an ice cold saturated aqueous sodium bicarbonate solution and the reaction product is extracted with chloroform. The chloroform extract is then first washed with water and then with saturated aqueous sodium chloride solution and afterwards dried with sodium sulphate. The chloroform is then evaporated off under reduced pressure. The residue is chromatographed on a silica gel column with hexane/ethyl acetate (99:1 to 98.2) as eluent. After fractional distillation of the practically pure chromatographic fractions, pure 1-bromo-4-isopentyloxy-butane is obtained, as a colourless oil. (Boiling point 40° to 46°0.03 mm Hg).

| Analysis: | $C_9H_{19}BrO$ | Molecular weight 223.2 | | |
|---|---|---|---|---|
| Calc. | C 48.4 % | H 8.6 % | Br 35.8 % | O 7.2 % |
| Found | 48.9 % | H 8.6 % | 35.4 % | 7.4 % |

EXAMPLE 24

1-Bromo-6-isopentyloxy-hexane 4.8 g (0.11 mol) of 55 % sodium hydride dispersion are added at 20°–40°C over the course of 1 hour, to 74 g (1.0 mol) of isopentyl alcohol. After stirring for 2 hours at 20°–25°C, 24.4 g (0.10 mol) of 1,6-dibromohexane are added dropwise over the course of 15 minutes. The mixture is stirred at 60°C for 16 hours, then filtered and the filtrate is taken up in ether. The ether solution is extracted with saturated sodium chloride slution, dried with sodium sulphate and evaporated at 40°C/18 mm Hg. After chromatography of the residue on silica gel with hexane/ethyl acetate (99:1) and subsequent distillation (B.P. 85°–87°/1 mm), 1-bromo-6-isopentyloxy-hexane is obtained as a slightly yellow clear liquid.

| Analysis: | $C_{11}H_{23}BrO$ | Molecular weight: 251.2 | |
|---|---|---|---|
| Calc. | C 52.6 % | H 9.2 % | Br 31.8 % |
| Found | 52.6 % | 9.3 % | 31.2 % |
| | O 6.4 % | | |
| | 6.8 % | | |

EXAMPLE 25

1-Bromo-6-isopropoxy-hexane

The above compound is produced in analogous manner to that described in Example 24, but using isopropanol in the place of isopentyl alcohol.

| Analysis: | $C_9H_{19}BrO$ | Molecular weight: 223.2 | | |
|---|---|---|---|---|
| Calc. | C 48.4 % | H 8.6 % | Br 35.8 % | O 7.2 % |
| Found | 48.7 % | 8.4 % | 35.9 % | 7.6 % |

EXAMPLE 26

1-Bromo-5-isopropoxy-pentane

The above compound is produced in analogous manner to that described in Example 25, but using 1,5-dibromopentane in the place of 1,6-dibromohexane. B.P.: 80.5°–81.5°/12 mm Hg

| Analysis: | $C_8H_{17}BrO$ | Molecular weight: 209.1 | | |
|---|---|---|---|---|
| Calc. | C 45.9 % | H 8.2 % | Br 38.2 % | O 7.7 % |
| Found | 46.1 % | 8.2 % | 38.7 % | 8.0 % |

EXAMPLE 27

1-Bromo-5-sec-butoxy-3-methylpentane

To 115 g (1.56 mols) of sec-butanol are added over the course of 15 minutes, 2.0 g (0.087 mol) of finely cut sodium. The mixture is stirred at 60° for 2 hours in order to dissolve the sodium completely. After the addition of 21.2 g (0.087 mol) of 1,5-dibromo-3-methylpentane, the mixture is stirred at 60°, over the source of 18 hours. The precipitated sodium bromide is filtered off and the excess sec-butanol is distilled off. The residue is taken up in 300 cc of ether, washed three times with water and once with saturated sodium chloride solution, dried over magnesium sulphate and evaporated at 40°/20 mm Hg. After chromatography of the residue on silica gel with hexane/ethyl acetate (98,5:1,5) and subsequent fractional distillation in a high vacuum, 1-bromo-5-sec-butoxy-3-methyl-pentane is obtained as a colourless liquid. B.P.: 104° – 106°/13 mm Hg

EXAMPLE 28

1-Bromo-6-sec-butoxy-hexane

The above compound is produced in analogous manner to that described in Example 27, but using 1,6-dibromohexane in the place of 1,5-dibromo-3-methylpentane. B.P.: 105° – 107°/12 mm Hg.

| Analysis: | $C_{10}H_{21}BrO$ | Molecular weight: 237.2 | |
|---|---|---|---|
| Calc. | C 50.6 % | H 8.9 % | Br 33.7 % |
| Found | 51.0 % | 8.5 % | 33.6 % |

EXAMPLE 29

1-Bromo-6-isopropoxy-4-methyl-3-hexene

A solution of 46 g (0.354 mol) of 4-isopropxy-2-butanone in 100 cc of absolute tetrahydrofuran is added dropwise over the course of 10 minutes at 5°C, under nitrogen and whilst stirring, to the Grignard reagent, producted from 9.06 g (0.378 mol) of magnesium and 42.8 g (0.389 mol) of cyclopropyl bromide in 460 cc of absolute tetrahydrofuran. The reaction mixture is stirred for 20 hours at room temperature and saturated ammonium chloride solution and ice are subsequently added. The mixture is extracted with ether. The ether extract is washed with saturated sodium chloride solution, dried over sodium sulphate and evaporated. The obtained 2-cyclopropyl-4-isopropoxy-2-butanol may be reacted to the bromide without further purification.

19 cc of 48 % hydrobromic acid are added dropwise, whilst stirring, at 0°C, over the course of 15 minutes, to 27.7 g of crude 2-cyclopropyl-4-isopropoxy-2-butanol. The mixture is stirred at 0°–5°C over the source of 30 minutes, and subsequently extracted with ether. The ether extract is washed with water, saturated sodium bicarbonate solution and saturated sodium chloride solution, dried over sodium sulphate and evaporated. The residue (20.2 g) is chromatographed with hexane/ethyl acetate (98:2) and (95:5) on silica gel. A chromatographically pure cis, trans isomeric mixture of 1-bromo-6-isopropoxy-4-methyl-3-hexene is obtained, $n_D^{20} = 1.4802$.

| Analysis: | $C_{10}H_{19}BrO$ | Molecular weight: 235.2 | |
|---|---|---|---|
| Calc. | C 51.1 % | H 8.1 % | Br 34.0 % |
| Found | 51.1 % | 8.3 % | 33.2 % |

EXAMPLE 30

1-Bromo-5-isopropoxy-3-methyl-pentane 13.6 g (0.05 mol) of phosphorus tribromide and 2.47 g (0.03 mol) of pyridine are mixed and cooled to 0°–5°C. 20 g (0.125 mol) of 5-isopropoxy-3-methyl-1-pentanol are added dropwise, whilst stirring, over the course of 1 hour. The turbid mixture is then heated to 25°C and after 2 hours at 12 mm Hg, the reaction mixture is distilled into a receiver containing ice cold saturated sodium bicarbonate solution. (B.P.: 92°–103°/12 mm). The distillate is taken up in ether, successively washed with saturated sodium bicarbonate solution, water, 2N sulphuric acid, water, dried with sodium sulphate and evaporated. The residue is distilled, whereby 1-bromo-5-isopropoxy-3-methyl-pentane is obtained. B.P.: 92°–95°/12 mm Hg.

| Analysis: | $C_9H_{19}BrO$ | Molecular weight: 223.2 | | |
|---|---|---|---|---|
| Calc. | C 48.4 % | H 8.6 % | Br 35.8 % | O 7.2 % |
| Found | 48.3 % | 8.6 % | 36.1 % | 7.3 % |

Compounds of formula IX

The production of the compound of formula IX may be effected in accordance with the following Example 31.

EXAMPLE 31

6-Isopropoxyhexanal 7.5 cc (0.132 mol) of dimethyl sulphide are added dropwise at 0°, whilst stirring and under nitrogen, to a solution of 13.4 g (0.10 mol) of N-chlorosuccinimide in 250 cc of absolute toluene. A white precipitate is formed. The reaction mixture is subsequently cooled to −25° and a solution of 8.0 g (0.05 mol) of 6-isopropoxyhexanol in 25 cc of absolute toluene is added over the course of 15 minutes. After stirring at −25° for 90 minutes, a solution of 7.5 g (0.074 mol) of triethylamine in 25 cc of toluene is added over the course of 15 minutes to the white suspension. The cooling bath is then separated and after 10 minutes 500 cc of ether are added. The organic phase is washed with 1% aqueous hydrochloric acid, water and saturated sodium chloride solution, dried over magnesium sulphate and evaporated at 30°/20 mm Hg. After fractional distillation almost pure 6-isopropoxyhexanol is obtained (B.P. 90–93°/15 mm Hg). Said compound may be used for the production of 1-(7-isopropoxy-1-heptenyl)-4 -nitrobenzene without further purification.

Compounds of formula XVIII

The alcohols of formula XVIII may, for example be produced in accordance with Example 32–35:

EXAMPLE 32

4-Isopentyloxy-1-butanol 36.0 g (0.40 mol) of 1,4-butandiol are added over the course of 20 minutes of a suspension of 12.20 g (0.279 mol) of 55 % sodium hydride in 400 cc of absolute 1,2-dimethoxyethane. The mixture is stirred at 55°C for 2 hours. After this period, 40.2 g (0.266 mol) of isopentyl bromide are added dropwise at 55°, over the course of 20 minutes, and the mixture is then stirred at 60° for 48 hours. The reaction mixture is cooled, filtered and the filtrate is evaporated at 40°/12 mm Hg. The residue is distilled at 0.9 mm Hg and for further purification the fraction, having a B.P. of 75° – 88°/0.09 mm Hg, is taken up in ether and washed with water. 4-Isopentyloxy-1-butanol is obtained as a gas-chromatographically pure oil.

| Abalysis: | $C_9H_{20}$ | Molecular weight 160.3 | | |
|---|---|---|---|---|
| Calc. | C 67.5 % | H 12.6 % | O 20.0 % | |
| Found | 67.3 % | 12.5 % | 19.8 % | |

The alcohols, useful as intermediate products for the production of the aldehydes of general formula IX, may be produced in analogous manner to the process described for the production of the alcohols of general formula XVIII.

EXAMPLE 33

6-Isopropoxyhexanol

The above compound is produced in analogous manner to that described in Example 32, but using 1,6-hexandiol in the place of 1,4-butanol and isopropylbromide in the place of isopentylbromide. B.P.: 73°–75°/0.22 mm Hg.

| Analysis: | $C_9H_{20}O_2$ | Molecular weight: 160.3 |
|---|---|---|
| Calc. | C 67.5 % | H 12.6 % |
| Found | 67.4 % | 12.6 % |

Compound of formula XVIII

The production of the alcohols of formula XVIII by hydrogenation of the compound of formula XXII and subsequent removal of the protecting group of the hydrogenation product may, for example. be effected in accordance with Example 34:

EXAMPLE 34

5-Isopropoxy-3-methyl-1-pentanol 600 g of 1-acetoxy-5-isopropoxy-3-methyl-2-pentene are hydrogenated in 2000 cc of ethanol with 60 g of Raney nickel at 71 atmospheric pressure and 70°C for 24 hours. After this period, another 30 g of catalyst are added and hydrogenation is effected under the same conditions for a further 20 hours. After filtration, the reaction mixture is evaporated and the residue is distilled. Gas-chromatographically pure 1-acetoxy-5-isopropoxy-3-methyl-pentane is obtained. B.P.: 106°–108°/12 mm Hg. $n_D^{20} = 1.4286$

| Analysis: | $C_{11}H_{22}O_3$ | Molecular weight: 202.3 |
|---|---|---|
| Calc. | C 65.3 % | H 11.0 % |
| Found | 65.0 % | 10.8 % |

21 g (0.375 mol) of potassium hydroxide are added to 50.5 g (0.25 mol) of 1-acetoxy-5-isopropoxy-3-methyl-pentane, dissolved in 300 cc of methanol. The mixture is boiled at reflux for 1 hour, concentrated by evaporation to 20 cc at 30°C and 150 cc of water are added. The mixture is extracted with chloroform. The chloroform extract is washed with water, dried with sodium sulphate and evaporated. The residue is distilled at 20 mm Hg. Gas-chromatographically pure 5-isopropoxy-3-methyl-1-pentanol, having a B.P. of 118°–120°/20 mm Hg, is obtained. $n_D^{20} = 1.4371$.

| Analysis: | $C_9H_{20}O_2$ | Molecular weight: 160.3 | |
|---|---|---|---|
| Calc. | C 67.5 % | H 12.6 % | O 20.0 % |

-continued

| | | | |
|---|---|---|---|
| Found | 67.3 % | 12.7 % | 20.2 % |

The production of the compounds of general formula XXII from the compound of general formula XXVI may, for example, be effected in accordance with Example 35:

EXAMPLE 35

1-Acetoxy-5-isopropoxy-3-methyl-2-pentene

A mixture of 450 g (4.6 mols) of potassium acetate and 637 g (3.6 mols) of 1-chloro-5-isopropoxy-3-methyl-2-pentene in 3000 cc of dimethylformamide is stirred at room temperature for 24 hours and then at 50°C for 4 hours. The reaction mixture is filtered, and solvent is distilled off at 1.4 mm Hg and the residue is fractionally distilled. A cis/trans mixture of 1-acetoxy-5-isopropoxy-3-methyl-2-pentene is obtained. B.P.: 122°–126°/18 mm Hg.

| Analysis: | $C_{11}H_{20}O_3$ | | Molecular weight: | 200.3 |
|---|---|---|---|---|
| Calc. | C 66.0 % | H 10.1 % | | O 24.0 % |
| Found | 65.9 % | 10.2 % | | 23.1 % |

Compounds of formula XXVI

The production of the compounds of general formula XXVI from the compound of general formulae XXIV and XXIII may, for example, be effected in accordance with Example 36:

EXAMPLE 36

1-Chloro-5-isopropoxy-3-methyl-2-pentene 32.4 g of chloromethyl-isopropyl ether are added dropwise at 0°C, over the course of 40 minutes, whilst stirring, to 20.4 g (0.3 mol) of isoprene and 0.3 g of zinc chloride. The mixture is subsequently stirred at room temperature over the course of 24 hours. The reaction mixture is taken up in ether, successively washed with water, sodium bicarbonate solution and water. The ether phase is dried with sodium sulphate, the ether is distilled off and the residue is distilled at 12 mm Hg, whereby 1-chloro-5-isopropoxy-3-methyl-2-pentene is obtained, B.P.: 86°–92°/12 mm Hg. $n_D^{20} = 1.4553$

| Analysis: | $C_9H_{17}ClO$ | | Molecular weight: | 176.7 |
|---|---|---|---|---|
| Calc. | C 61.2 % | H 9.7 % | | Cl 20.1 % |
| Found | 61.3 % | 9.6 % | | 20.3 % |

What is claimed is:
1. A compound of the formula:

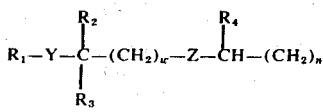

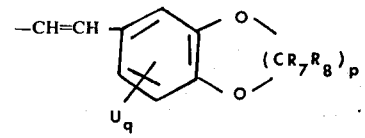

wherein
$R_1$ is alkyl of 1 to 6 carbon atoms, alkenyl of 3 to 6 carbon atoms, alkynyl of 3 to 6 carbon atoms, cycloalkyl of 5 to 7 carbon atoms or cycloalkyl of 5 to 7 ring carbon atoms substituted by alkyl of 1 to 6 carbon atoms,
$R_2$, $R_3$ and $R_4$ are independently hydrogen or alkyl of 1 to 4 carbon atoms,
Z is $-CR_5=CH-$, $-CH=CR_5-$ or $-CHR_5-$,
$R_5$ is hydrogen or alkyl of 1 to 4 carbon atoms,
Y is oxygen or sulfur,
$w$ and $n$ are independently 0 to 4,
U is alkyl of 1 or 2 carbon atoms, alkoxy of 1 or 2 carbon atoms or alkylthio of 1 or 2 carbon atoms,
$R_7$ and $R_8$ are independently hydrogen or alkyl of 1 or 2 carbon atoms,
$p$ is 1, and
$q$ is 0 to 2.

2. A compound of claim 1, wherein $R_1$ is alkyl of 1 to 6 carbon atoms.
3. A compound of claim 2, wherein $R_7$ and $R_8$ are each hydrogen.
4. A compound of claim 3, wherein $q$ is zero.
5. A compound of claim 4, wherein Y is oxygen.
6. A compound of claim 5, wherein Z is $-CHR_5-$.
7. The compound of claim 6, which is 1-(6-isopropoxy-4-methyl-1-hexenyl)-3,4-methylenedioxybenzene.
8. The compound of claim 6, which is 1-(5-isopentyloxy-1-pentenyl)-3,4-methylenedioxylbenzene.
9. The compound of claim 6, which is 1-(7-isopentyloxy-1-heptenyl)-3,4-methylenedioxybenzene.
10. The compound of claim 6, which is 1-(7-isopropoxy-1-heptenyl)-3,4-methylenedioxybenzene.
11. The compound of claim 6, which is 1-(6-isopropoxy-1-hexenyl)-3,4-methylenedioxybenzene.
12. The compound of claim 6, which is 1-(6-sec.-butoxy-4-methyl-1-hexenyl)-3,4-methylenedioxybenzene.
13. The compound of claim 6, which is 1-(7-sec.-butoxy-1-heptenyl)-3,4-methylenedioxylbenzene.
14. The compound of claim 6, which is 1-(8-methoxy-4,8-dimethyl-1-nonenyl)-3,4-methylenedioxybenzene.
15. A compound of claim 5, wherein Z is $-CR_5=CH-$.
16. The compound of claim 15, which is 1-(7-isopropoxy-5-methyl-1,4-heptadienyl)-3,4-methylenedioxybenzene.

* * * * *